(12) United States Patent
Patel

(10) Patent No.: US 8,158,113 B2
(45) Date of Patent: *Apr. 17, 2012

(54) GUAR GUM CONTAINING COMPOUNDS

(75) Inventor: Amit Patel, Dallas, TX (US)

(73) Assignee: Mary Kay Inc., Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/219,324

(22) Filed: Aug. 26, 2011

(65) Prior Publication Data

US 2011/0311468 A1    Dec. 22, 2011

Related U.S. Application Data

(63) Continuation of application No. 12/144,342, filed on Jun. 23, 2008, now Pat. No. 8,029,771.

(60) Provisional application No. 60/947,199, filed on Jun. 29, 2007.

(51) Int. Cl.
*A61K 8/00* (2006.01)
*C06B 37/00* (2006.01)

(52) U.S. Cl. ......................... 424/63; 536/114

(58) Field of Classification Search ................. None
See application file for complete search history.

(56) References Cited

U.S. PATENT DOCUMENTS

| | | | |
|---|---|---|---|
| 5,961,998 A | 10/1999 | Arnaud et al. | 424/401 |
| 6,060,044 A * | 5/2000 | Cretois et al. | 424/70.12 |
| 6,383,505 B1 | 5/2002 | Kaiser et al. | 424/407 |
| 6,436,413 B1 | 8/2002 | Gers-Barlag et al. | 424/401 |
| 6,464,965 B1 | 10/2002 | Chiarelli et al. | 424/59 |
| 6,511,655 B1 | 1/2003 | Muller et al. | 424/59 |
| 6,793,940 B2 | 9/2004 | Tournilhac et al. | 424/707 |
| 6,811,770 B2 | 11/2004 | Ferrari et al. | 424/64 |
| 6,875,245 B2 | 4/2005 | Pavlin | 44/275 |
| 6,902,722 B2 | 6/2005 | Candau et al. | 424/59 |
| 6,958,148 B1 | 10/2005 | Green et al. | 424/94.5 |
| 6,994,846 B2 | 2/2006 | L'Alloret | 424/78.18 |
| 7,030,985 B2 | 4/2006 | Jager-Lezer et al. | 356/402 |
| 2002/0086039 A1 | 7/2002 | Lee et al. | 424/401 |
| 2003/0118531 A1 | 6/2003 | Kolodziej et al. | 424/63 |
| 2003/0185780 A1 | 10/2003 | Ferrari et al. | 424/70.11 |
| 2003/0215479 A1 | 11/2003 | Sendelbach et al. | 424/401 |
| 2003/0235553 A1 | 12/2003 | Lu et al. | 424/70.122 |
| 2004/0096404 A1 | 5/2004 | Zofchak et al. | 424/59 |
| 2004/0176273 A1 | 9/2004 | Bissett | 514/275 |
| 2004/0191191 A1 | 9/2004 | Ehlis et al. | 424/59 |
| 2004/0202634 A1 | 10/2004 | L'Alloret | 424/70.16 |
| 2004/0223987 A1 | 11/2004 | Ferrari | 424/401 |
| 2004/0234558 A1 | 11/2004 | O'Connor et al. | 424/401 |
| 2005/0053632 A1 | 3/2005 | Schafer et al. | 424/401 |
| 2005/0129641 A1 | 6/2005 | Arnaud et al. | 424/63 |
| 2005/0214333 A1 | 9/2005 | Lanzendoerfer et al. | 424/401 |
| 2005/0271609 A1 | 12/2005 | Fei et al. | 424/65 |
| 2006/0008433 A1 | 1/2006 | Chevalier | 424/61 |
| 2006/0013791 A1 | 1/2006 | Shimizu et al. | 424/70.12 |
| 2006/0018866 A1 | 1/2006 | Kawakami et al. | 424/70.27 |
| 2006/0074108 A1 | 4/2006 | Gupta | 514/332 |
| 2006/0110345 A1 | 5/2006 | Lu et al. | 424/64 |
| 2006/0110379 A1 | 5/2006 | Green et al. | 424/94.5 |
| 2006/0110415 A1 | 5/2006 | Gupta | 424/401 |
| 2006/0115440 A1 | 6/2006 | Arata et al. | 424/65 |
| 2006/0127341 A1 | 6/2006 | Lion et al. | 424/70.16 |
| 2006/0134038 A1 | 6/2006 | De La Poterie et al. | 424/70.1 |
| 2006/0134053 A1 | 6/2006 | L'Alloret | 424/70.16 |
| 2006/0172904 A1 | 8/2006 | Bonafos | 510/130 |

FOREIGN PATENT DOCUMENTS

WO    WO 02/058642    8/2002

OTHER PUBLICATIONS

Office Communication issued in U.S. Appl. No. 12/144,342, dated Apr. 22, 2011.

* cited by examiner

*Primary Examiner* — Patricia A Duffy
*Assistant Examiner* — Dennis J Parad
(74) *Attorney, Agent, or Firm* — Fulbright & Jaworski L.L.P.

(57) ABSTRACT

Disclosed is a method of reducing the appearance of coloring streaks in a composition that has a colorant comprising adding a guar gum containing compound to said composition.

5 Claims, No Drawings

GUAR GUM CONTAINING COMPOUNDS

CROSS-REFERENCE TO RELATED APPLICATIONS

This application is a continuation application of U.S. application Ser. No. 12/144,342, filed Jun. 23, 2008, which claims the benefit of U.S. Provisional Application No. 60/947,199, filed Jun. 29, 2007. The contents of the referenced applications are incorporated by reference.

BACKGROUND OF THE INVENTION

A. Field of the Invention

The present invention relates generally to a compound that can be used as a dispersing agent or suspending agent in compositions. The compound can include a guar gum backbone that has selected groups attached to the backbone.

B. Description of Related Art

Cosmetic compositions come in a wide variety of colors or shades. This variety is often exhibited in products such as lipsticks, eyeliners, mascara, and blushes. Colorants such as pigments can be used to create these different colors or shades.

A problem associated with the use of colorants is that they tend to agglomerate together in a composition. This agglomeration can cause the color of the composition to appear blotchy. One attempt to solve this agglomeration problem is to either treat the surface of the colorants or add a compound to the composition that interacts with the colorant to more efficiently disperse the colorant throughout the composition. Although these type of treatments and compounds have been shown to decrease agglomeration, such treatments and compounds oftentimes inefficiently disperse such colorants. This can cause the composition to have a streaky or non-homogenous color appearance.

SUMMARY OF THE INVENTION

The present invention overcomes deficiencies in the art. In a non-limiting aspect, the invention relates generally to compounds that can be used as dispersing and/or suspending agents. In certain embodiments, the compounds can include a guar gum backbone that includes at least one —H, —OH, an alkoxy group, an acyloxy group, an amino group, an amido group, a sulfate group, a sulfonate group, a phosphate group, a phosphonate group, or a silicone group attached to the backbone. In one non-limiting aspect, the groups attached to the guar gum backbone can be alkyl benzoate groups, urethane groups, surfactants, silicone groups, ester groups, or combinations thereof. The ratio of the guar gum backbone to a particular group or a combination of groups attached to the backbone can vary to obtain a desired characteristic of the compound. By way of example, the ratio of the guar gum backbone to a particular group or combination of groups attached to the backbone can be about 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 50:1, 60:1, 70:1, 80:1, 90:1, 100:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:50, 1:60, 1:70, 1:80, 1:90, 1:100, or more or any number derivable therein, by weight (e.g., molecular weight) of the total compound. Generic and specific structures of these compounds are disclosed throughout this specification and incorporated into this section by reference.

In certain aspects, the compounds can have any desired molecule weight. For instance, certain compounds of the present invention can have an average molecular weight between 5 kilodaltons and 8,000 kilodaltons (e.g., 5, 10, 15, 20, 230, 40, 50, 60, 70, 80, 90, 100, 500, 1000, 1500, 2000, 2500, 3000, 3500, 4000, 4500, 5000, 5500, 6000, 6500, 7000, 7500, 8000, or more or any range or integer derivable therein). In one embodiment, at least 1, 2, 3, 4, 5, 6, 7, 8, 9, 10, 20, 30, 40, 50, 60, 70, 80, 90, 91, 92, 93, 94, 95, 96, 97, 98, 99% or more of the molecular weight of the compound can be attributed to the guar gum backbone, a group attached to the backbone, or a combination of groups to the backbone.

The compounds can be used as dispersing agents, wetting agents, or suspending agents in compositions. In certain aspects, the compounds are capable of decrease an amount of a colorant in a cosmetic composition by at least 1, 5, 10, 15, 20, 30, 40, 50, 60, 70, 80, 90 percent, while maintaining the cosmetic characteristics of the composition.

In other aspects, the compounds can be applied to the surface of a colorant, solid, particle, powder, etc. Non-limiting examples include iron oxides, micas, and pearlescent pigments. The compounds can be attached to such surfaces by known methods (e.g., spray techniques, immersion techniques. In certain aspects, the compounds are chemically bonded to the surface (e.g., covalent bonds, ionic bonds, etc.). In other aspects, the compounds can be attached to the surface by the way of an adhesive.

Another aspect of the present invention includes a composition that includes the guar gum containing compounds disclosed throughout this specification. The compositions can include a colorant, a particle, a solid, a powder etc. The composition can be cosmetic compositions, pharmaceutical compositions, ink compositions, paint compositions, etc. The composition can be topically applied to skin. The compositions can be included in a vehicle. Non-limiting examples of cosmetic vehicles are disclosed in other sections of this specification and are known to those of skill in the art. Examples of cosmetic vehicles include emulsions (e.g., oil-in-water and water-in-oil emulsions), creams, lotions, solutions (e.g., aqueous or hydro-alcoholic solutions), anhydrous bases (e.g., lipstick or a powder), gels, and ointments. In other non-limiting embodiments, the compositions of the present invention can be included in anti-aging, cleansing, or moisturizing products. The compositions can be anhydrous. In other aspects of the present invention, compositions can be storage stable or color stable, or both.

In certain embodiments, the compositions of the present invention can include from about 1% to about 99%, by weight or volume, of the guar gum containing compounds. It should be recognized, however, that the amount of the compounds in a composition can be modified below, within, or above this range based on the desired results (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 96, 97, 98, 99%, or more, by weight or volume of the composition). In certain embodiments, the compositions of the present invention can further include a colorant, a particle, a solid, a powder etc. In certain aspects, the ratio of any ingredient within the composition when compared to another ingredient can be from about 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 50:1, 60:1, 70:1, 80:1, 90:1, 100:1, or more or any number derivable therein, by weight or volume of the total composition. In other aspects, the ratio of any ingredient within the composition when compared to another ingredient can be from about 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:50, 1:60, 1:70, 1:80, 1:90, 1:100, or more or any number derivable therein, by weight or volume of the total composition. The compositions in non-limiting aspects can have a pH of about 6 to about 9. In other aspects, the pH can be 1, 2, 3, 4, 5, 6, 7, 8, 9, 10, 11, 12, 13, or 14. The compounds can be included in a hydrophobic phase e.g., oil phase, silicone phase, etc.) of a composition. The compositions can include an effective amount of a compound to permit a high content (e.g., up to at least 30%) of a colorant in the composition or to obtain a transparent composition. It is also contemplated that the viscosity of the composition can be selected to achieve a desired result (e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000 cps, etc.).

Various methods for using the compounds are also disclosed. By way of example, a method of dispersing a colorant in a composition comprising adding a compound of the present invention to the composition, wherein the colorant is dispersed throughout the composition is disclosed. Other methods include a method of reducing the appearance of coloring streaks or undispersed colorants in a composition comprising adding a compound of the present invention to the composition, wherein the appearance of coloring streaks or undispersed colorants in the composition is reduced when compared to a composition that does not include such a compound. Also disclosed is a method of increasing the viscosity of a composition comprising adding a compound of the present invention to the composition, wherein the viscosity of the composition is increased when compared to a composition that does not include such a compound. A method of suspending an agent in a composition comprising adding a compound of the present invention to the composition is also disclosed. Also contemplated is a method of decreasing the amount of a colorant in a composition while maintaining the color of the composition comprising adding the compound of claim 1 to the composition, wherein the compound allows for the removal of at least 10% of the colorant from the composition while maintaining the color of the composition when compared to the same composition that does not include such a compound. A method of providing a homogenous color to a composition comprising adding a compound of the present invention to the composition is disclosed. A method of increasing the intensity of the color of a composition comprising adding a compound of the present invention to the composition, where the color intensity of the composition is increased when compared to a composition that does not include such a compound is also disclosed. There is also disclosed a method of obtaining a transparent composition comprising adding a compound of the present invention to the composition. In another aspect, there is disclosed a method of increasing the dispersibility or decreasing the agglomeration of a colorant, a particle, a solid, a powder, etc. in a composition comprising applying a compound of the present invention to the surface of the colorant, particle, solid, powder, etc., wherein the dispersibility of the colorant, particle, solid, powder, etc. in the composition is increased or the agglomeration of the same is decreased when compared with the dispersibility or agglomeration of such a colorant, particle, solid, powder, etc., in a composition that does not have the compound attached to its surface.

Also contemplated are methods of treating or preventing a skin condition comprising topical application of a composition of the present invention to skin, wherein the topical application of the composition treats the skin condition. Non-limiting examples of skin conditions include pruritus, spider veins, lentigo, age spots, senile purpura, keratosis, melasma, blotches, fine lines or wrinkles, nodules, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, impetigo, erysipelas, erythrasma, eczema, and other inflammatory skin conditions. In certain non-limiting aspects, the skin condition can be caused by exposure to UV light, age, irradiation, chronic sun exposure, environmental pollutants, air pollution, wind, cold, heat, chemicals, disease pathologies, smoking, or lack of nutrition. The skin can be facial skin or non-facial skin (e.g., arms, legs, hands, chest, back, feet, etc.). The method can further comprise identify a person in need of skin treatment. The person can be a male or female.

Also contemplated are kits that include the compositions of the present invention. In certain embodiments, the composition is comprised in a container. The container can be a bottle, dispenser, or package. The container can dispense a predetermined amount of the composition. In certain aspects, the compositions is dispensed in a spray or mist, dollop, or liquid. The container can include indicia on its surface. The indicia can be a word, an abbreviation, a picture, or a symbol.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a foundation, a night cream, a lipstick, a cleanser, a toner, a sunscreen, a mask, or an anti-aging product.

It is contemplated that any embodiment discussed in this specification can be implemented with respect to any method or composition of the invention, and vice versa. Furthermore, compositions of the invention can be used to achieve methods of the invention.

"Alkyl" includes straight-chain alkyl groups, branched-chain alkyl groups, cycloalkyl (alicyclic) groups, alkyl heteroatom-substituted cycloalkyl groups, cycloalkyl heteroatom-substituted alkyl groups, heteroatom-unsubstituted $C_n$-alkyl, and heteroatom-substituted $C_n$-alkyl groups.

"Heteroatom-unsubstituted $C_n$-alkyl" includes a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, a heteroatom-unsubstituted $C_1$-$C_{10}$-alkyl has 1 to 10 carbon atoms. The groups, —$CH_3$, —$CH_2CH_3$, —$CH_2CH_2CH_3$, —$CH(CH_3)_2$, —$CH(CH_2)_2$ (cyclopropyl), —$CH_2CH_2CH_2CH_3$, —$CH(CH_3)CH_2CH_3$, —$CH_2CH(CH_3)_2$, —$C(CH_3)_3$, —$CH_2C(CH_3)_3$, cyclobutyl, cyclopentyl, and cyclohexyl, are all non-limiting examples of heteroatom-unsubstituted alkyl groups.

"Heteroatom-substituted $C_n$-alkyl" includes a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted $C_1$-$C_{10}$-alkyl has 1 to 10 carbon atoms. The following groups are all non-limiting examples of heteroatom-substituted alkyl groups: trifluoromethyl, —$CH_2F$, —$CH_2Cl$, —$CH_2Br$, —$CH_2OH$, —$CH_2OCH_3$, —$CH_2OCH_2CH_3$, —$CH_2OCH_2CH_2CH_3$, —$CH_2OCH(CH_3)_2$, —$CH_2OCH(CH_2)_2$, —$CH_2OCH_2CF_3$, —$CH_2OCOCH_3$, —$CH_2NH_2$, —$CH_2NHCH_3$, —$CH_2N(CH_3)_2$, —$CH_2NHCH_2CH_3$, —$CH_2N(CH_3)CH_2CH_3$, —$CH_2NHCH_2CH_2CH_3$, —$CH_2NHCH(CH_3)_2$, —$CH_2NHCH(CH_2)_2$, —$CH_2N(CH_2CH_3)_2$, —$CH_2CH_2F$, —$CH_2CH_2Cl$, —$CH_2CH_2Br$, —$CH_2CH_2I$, —$CH_2CH_2OH$, $CH_2CH_2OCOCH_3$, —$CH_2CH_2NH_2$, —$CH_2CH_2N(CH_3)_2$, —$CH_2CH_2NHCH_2CH_3$, —$CH_2CH_2N(CH_3)CH_2CH_3$, —$CH_2CH_2NHCH_2CH_2CH_3$, —$CH_2CH_2NHCH(CH_3)_2$, —$CH_2CH_2NHCH(CH_2)_2$, —$CH_2CH_2N(CH_2CH_3)_2$, —$CH_2CH_2NHCO_2C(CH_3)_3$, and —$CH_2Si(CH_3)_3$.

"Alkoxy" includes a group having the structure —OR, where R is an alkyl group.

"Acyl" includes straight-chain acyl groups, branched-chain acyl groups, cycloacyl (alicyclic) groups, acyl heteroatom-substituted cycloacyl groups, cycloacyl heteroatom-substituted acyl groups, heteroatom-unsubstituted $C_n$-acyl, and heteroatom-substituted $C_n$-acyl groups.

"Heteroatom-unsubstituted $C_n$-acyl" refers to a radical, having a single carbon atom of a carbonyl group as the point of attachment, further having a linear or branched, cyclic or acyclic structure, further having a total of n carbon atoms, 1 or more hydrogen atoms, a total of one oxygen atom, and no additional heteroatoms. For example, a heteroatom-unsubstituted $C_1$-$C_{10}$-acyl has 1 to 10 carbon atoms. The groups, —CHO, —$COCH_3$, —$COCH_2CH_3$, —$COCH_2CH_2CH_3$, —$COCH(CH_3)_2$, —$COCH(CH_2)_2$, —$COC_6H_5$, —$COC_6H_4CH_3$, —$COC_6H_4CH_2CH_3$, —$COC_6H_4CH_2CH_2CH_3$, —$COC_6H_4CH(CH_3)_2$, —$COC_6H_4CH(CH_2)_2$, and —$COC_6H_3(CH_3)_2$, are non-limiting examples of heteroatom-unsubstituted acyl groups.

"Heteroatom-substituted $C_n$-acyl" refers to a radical, having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-acyl has 1 to 10 carbon atoms. The term heteroatom-substituted acyl includes carbamoyl, thiocarboxylate, and thiocarboxylic acid groups. The groups, —$COCH_2CF_3$, —$CO_2H$, —$CO_2CH_3$, —$CO_2CH_2CH_3$, —$CO_2CH_2CH_2CH_3$, —$CO_2CH(CH_3)_2$, —$CO_2CH(CH_2)_2$, —$CONH_2$, —$CONHCH_3$, —$CONHCH_2CH_3$, —$CONHCH_2CH_2CH_3$, —$CONHCH(CH_3)_2$, —$CONHCH(CH_2)_2$, —$CON(CH_3)_2$, —$CON(CH_2CH_3)CH_3$, —$CON(CH_2CH_3)_2$ and —$CONHCH_2CF_3$, are examples heteroatom-substituted acyl groups.

"Acyloxy" includes a group having the structure —OR, where R is an acyl group.

"Amido" includes N-alkyl-amido, N-aryl-amido, N-aralkyl-amido, acylamino, alkylcarbonylamino, arylcarbonylamino, ureido groups, heteroatom-unsubstituted $C_n$-amido, or heteroatom-substituted $C_n$-amido.

"Heteroatom-unsubstituted $C_n$-amido" includes a radical, having a single nitrogen atom as the point of attachment, further having a carbonyl group attached via its carbon atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, a heteroatom-unsubstituted $C_1$-$C_{10}$-amido has 1 to 10 carbon atoms.

"Heteroatom-substituted $C_n$-amido" includes a radical, having a single nitrogen atom as the point of attachment, further having a carbonyl group attached via its carbon atom to the nitrogen atom, further having a linear or branched, cyclic or acyclic structure, further having a total of n aromatic or nonaromatic carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-amido has 1 to 10 carbon atoms.

"Sulfonate" groups includes the general formula $RSO_2O^-$, where R is an organic group, including any of those identified throughout the specification.

"Sulfate" groups includes the general formula $ROSO_2O^-$ where R is independently —H or an organic group, including any of those identified throughout the specification.

"Phosphonate" groups includes the general formula $OP(OR)_2R$ where R is independently —H or an organic group, including any of those identified throughout the specification.

"Phosphate" groups includes the general formula $OP(OR_3)$ where R is independently —H or an organic group, including any of those identified throughout the specification.

The term "about" or "approximately" are defined as being close to as understood by one of ordinary skill in the art, and in one non-limiting embodiment the terms are defined to be within 10%, within 5%, within 1%, and/or within 0.5%.

The terms "inhibiting," "preventing," or "reducing," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

The guar gum containing compounds of the present invention have a guar gum backbone with selected R groups attached to the backbone. Guar Gum is a glactomannan polymer that can be extracted from the seed of the leguminous shrub *Cyamopsis tetragonoloba*. This plant is typically cultivated in India, Pakistan, and southwestern U.S. The CAS registry number for guar gum is 9000-30-0. Guar gum is commercially available from a variety of sources (e.g., Tic Gums—Belcamp Md., and Rhodia Inc—Cranbury N.J.). Non-limiting examples of R groups include —H, —OH, an alkoxy group, an acyloxy group, an amino group, an amido group, a sulfate group, a sulfonate group, a phosphate group, a phosphonate group, or a silicone group. The selected R groups can modify or provide desired characteristics to the guar gum compound. By way of example only, some desired characteristics include dispersion and/or suspension capabilities when the modified compound is used in a given composition or a phase of a composition.

When the compounds of the present invention are used as a dispersion agent, they can be used to disperse colorants or other solid ingredients efficiently throughout the composition or a phase of the composition (e.g., a hydrophobic phase of a water-in-oil or oil-in-water emulsion). An advantage of having efficient dispersion of a colorant is that it can reduce the appearance of undeveloped colors in the composition. The composition can have a homogenous color appearance. Because of the efficient dispersion, more colorant can be added to the composition without affecting the stability of the composition which can be useful in obtaining a true or more intense, vivid, or vibrant color. When used as a suspending agent, the compounds can effectively modify the viscosity of the composition. For instance, the compounds can be used to increase the viscosity of a composition to achieve a desired rheological characteristic.

These and other aspect of the invention are described in further non-limiting detail below.

A. Guar Gum Containing Compounds

The guar gum containing compounds of the present invention can include a guar gum backbone that includes at least one —H, —OH, an alkoxy group, an acyloxy group, an amino group, an amido group, an ester group, a sulfate group, a sulfonate group, a phosphate group, a phosphonate group, a silicone group, a surfactant, a urethane group (including polyurethanes) attached to the backbone. A non-limiting generic structure of such a compound is illustrated below:

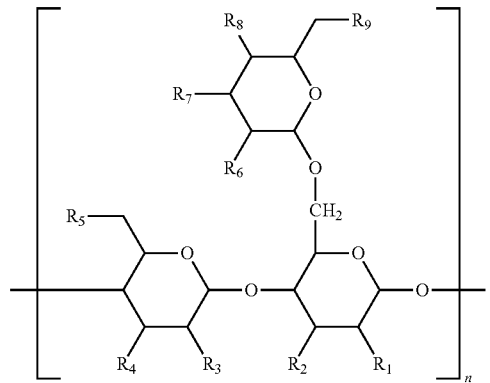

where: $R_1$ through $R_9$ are each independently —H, —OH, an alkoxy group, an acyloxy group, an amino group, an amido group, an ester group, a sulfate group, a sulfonate group, a phosphate group, a phosphonate group, a surfactant, a urethane group (including polyurethanes), or a silicone group having the following structure:

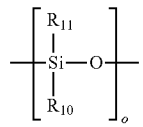

where $R_{10}$ though $R_{11}$ are each independently —H or an alkyl group; and n and o are independently integers from 2 to 10,000, where at least one of $R_1$ through $R_9$ is an alkoxy group, an acyloxy group, an amino group, an amido group, an ester group, a sulfate group, a sulfonate group, a phosphate group, a phosphonate group, a surfactant, a urethane group (including polyurethanes), or a silicone group.

Non-limiting examples of particular compounds of the present invention are illustrated below. These compounds have alkyl benzoate groups and/or silicone groups attached the guar gum backbone:

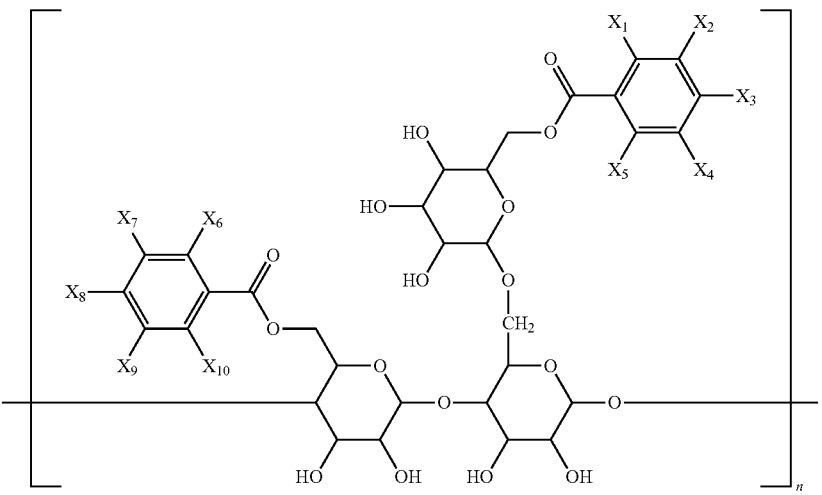

where $X_1$ though $X_{10}$ are each independently —H, —OH, or an alkyl group; and n is an integer from 2 to 100.

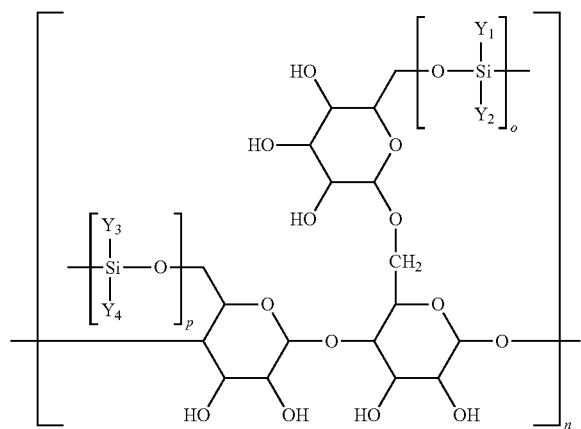

where $Y_1$ though $Y_4$ are each independently —H or an alkyl group; and n, o, and p are independently integers from 2 to 100.

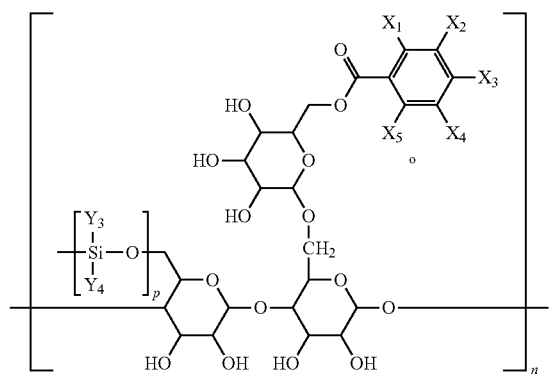

where $X_1$ though $X_5$ are each independently —H, —OH, or an alkyl group; $Y_3$ though $Y_4$ are each independently —H or an alkyl group; and n and p are independently integers from 2 to 100.

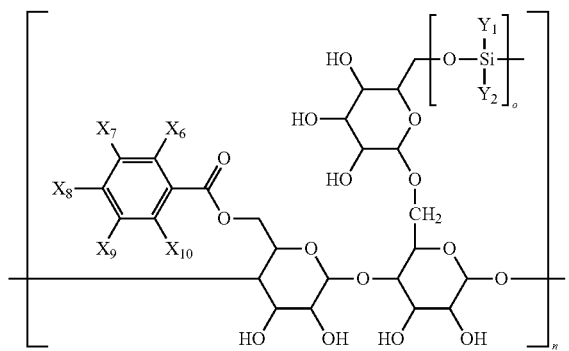

where $Y_1$ though $Y_2$ are each independently —H or an alkyl group; $X_6$ though $X_{10}$ are each independently —H, —OH, or an alkyl group; and n and o are independently integers from 2 to 100.

B. Modifications and Derivatives of the Guar Gum Compounds

Modifications or derivatives of the guar gum containing compounds disclosed throughout this specification are contemplated as being useful with the methods and compositions of the present invention. Derivatives and modifications may be prepared and the properties of such derivatives and modified compounds may be assayed for their desired properties by any method known to those of skill in the art. The modifications or derivatives can be made by using convention chemical synthesis techniques (see, e.g., Organic Chemistry, $5^{th}$ Ed.).

In certain aspects, "derivative" refers to a chemically modified guar gum containing compound that still retains the desired effects of the compound prior to the chemical modification. Such derivatives may have the addition, removal, or substitution of one or more chemical moieties on the guar gum backbone and/or the R groups that are attached to the backbone. Non-limiting examples of the modifications that can be made to these portions of the compounds include the addition or removal of alkyl groups, carboxyl groups, carbonyl groups, hydroxyl groups, nitro groups, amino groups, amide groups, azo groups, sulfate groups, sulfonate groups, sulfono groups, sulfhydryl groups, sulfonyl groups, sulfoxido groups, phosphate groups, phosphono groups, phosphoryl groups, and/or halide groups. Additional modifications can include an addition or a deletion of one or more atoms of the atomic framework, for example, substitution of an ethyl by a propyl or substitution of a phenyl by a larger or smaller aromatic group. In a cyclic or bicyclic structure, hetero atoms such as N, S, or O can be substituted into the structure instead of a carbon atom.

C. Compositions

The compounds of the present invention can be incorporated into all types of compositions (e.g., cosmetic and pharmaceutical compositions). A person of ordinary skill would recognize that the compositions can include any number of combinations of the guar gum containing compounds and/or additional ingredients, or derivatives thereof. The concentrations of the guar gum containing compounds and/or additional ingredients, or derivatives thereof, can vary for a given composition. This variation can oftentimes depend on the desired characteristics of the final composition. In non-limiting embodiments, for example, the compositions may include in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.5500%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the guar gum containing compound and/or additional ingredients, or derivatives thereof. In certain non-limiting aspects, the percentages can be calculated by weight or volume of the total composition. A person of ordinary skill in the art would understand that the concentrations can vary depending on the addition, substitution, and/or subtraction of the guar gum containing compound and additional ingredients, or derivatives thereof.

D. Additional Ingredients

In addition to the guar gum containing compounds disclosed throughout this specification, compositions of the present invention can include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. aloe vera, chamomile, cucumber extract, ginkgo biloba, ginseng, and rosemary), anti-microbial agents, anti-oxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, and manitol), exfoliants, water-proofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate). Non-limiting examples of some of these ingredients are provided in the following subsections.

a. Colorants

In certain non-limiting aspects, the guar gum containing compounds can be used to efficiently disperse colorants throughout a composition and/or a phase (e.g., water, oil, silicone phase) of the composition. Non-limiting examples of colorants that can be used in the context of the present invention include those known to a person of ordinary skill in the art (see, e.g., CTFA International Cosmetic Ingredient Dictionary and Handbook (2004)). For instance natural and synthetic pigments and lakes can be used. Examples of groups of pigments include carbon, cadmium, iron oxide, Prussian blue, chromium, cobalt, copper, titanium, ultramarine, zinc, clay earth, and organic pigments. Specific non-limiting examples of colorants include Aluminum Powder, Blue 1 Lake, Bronze Powder, Chromium Oxide Greens, Copper Powder, Ext. Yellow 7 Lake, Green 3 Lake, Orange 4 Lake, Orange 5 Lake, Orange 10 Lake, Pigment Blue 15, Pigment Blue 15:2, Pigment green 7, Pigment Orange 5, Pigment Red 4, Pigment Red 5, Pigment Red 48, Pigment Red 53, Pigment Red 53:1, Pigment Red 57, Pigment Red 57:1, Pigment Red 63:1, Pigment Red 64:1, Pigment Red 68, Pigment Red 83, Pigment Red 88, Pigment Red 90:1 Aluminum Lake, Pigment Red 112, Pigment Red 172 Aluminum Lake, Pigment Red 173 Aluminum Lake, Pigment Red 190, Pigment Violet 19, Pigment Yellow 1, Pigment Yellow 3, Pigment Yellow 12, Pigment Yellow 13, Pigment Yellow 73, Red 4 Lake, Red 6 Lake, Red 7 Lake, Red 21 Lake, Red 22 Lake, Red 27 Lake, Red 28 Lake, Red 30 Lake, Red 31 Lake, Red 33 Lake, Red 34 Lake, Red 36 Lake, Red 40 Lake, Sunset Yellow Aluminum Lake, Yellow 5 Lake, Yellow 6 Lake, Yellow 7 Lake, Yellow 10 Lake, and Zinc Oxide.

b. Preservatives

Non-limiting examples of preservatives that can be used in the context of the present invention include quaternary ammonium preservatives (e.g., polyquaternium-1), parabens (e.g., methylparabens and propylparabens), phenoxyethanol, benzyl alcohol, chlorobutanol, phenol, sorbic acid, thimerosal or combinations thereof.

c. Moisturizers

Non-limiting examples of moisturizing agents that can be used with the compositions of the present invention can be found in the International Cosmetic Ingredient Dictionary, 10$^{th}$ Ed., 2004. Examples include amino acids, chondroitin sulfate, diglycerin, erythritol, fructose, glucose, 1,2,6-hexanetriol, honey, hyaluronic acid, hydrogenated honey, hydrogenated starch hydrolysate, inositol, lactitol, maltitol, maltose, mannitol, natural moisturizing factor, salts of pyrollidone carboxylic acid, potassium PCA, sodium glucuronate, sodium PCA, sorbitol, sucrose, trehalose, urea, xylitol, glycerin, and petrolatum.

d. Emollients

Non-limiting examples of emollients include, but are not limited to, vegetable oils, mineral oils, silicone oils, synthetic and natural waxes, petrolatum, lanolin, aluminum magnesium hydroxide stearate (which can also function as a water repellent), and fatty acid esters. Non-limiting examples of vegetable oils include safflower oil, corn oil, sunflower seed oil, olive oil, or joboba esters.

e. Antioxidants

Non-limiting examples of antioxidants include, but are not limited to, acetyl cysteine, ascorbic acid, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, magnesium ascorbate, magnesium ascorbyl phosphate, methylsilanol ascorbate, natural botanical antioxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfate, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

f. Thickening Agents

Thickening agents, including thickener or gelling agents, include substances which that can increase the viscosity of a composition. Thickeners include those that can increase the viscosity of a composition without substantially modifying the efficacy of the ingredients within the composition. Thickeners can also increase the stability of the compositions of the present invention. Non-limiting examples of additional thickeners that are known to those of ordinary skill in the art can be used in the context of the present invention (e.g., U.S. Pat. Nos. 5,087,445; 4,509,949; 2,798,053; International Cosmetic Ingredient Dictionary and Handbook, $10^{th}$ Ed., 2004). Examples include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Examples of commercially available carboxylic acid polymers include carbomers, which are homopolymers of acrylic acid crosslinked with allyl ethers of sucrose or pentaerytritol (e.g., Carbopol™ 900 series from B.F. Goodrich).

g. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. The silicon containing compound can be a silicone oil such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in International Cosmetic Ingredient Dictionary, $10^{th}$ Ed., 2004 as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

2. Pharmaceutical Actives

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

E. Vehicles

Compositions of the present invention can be incorporated into all types of vehicles. Non-limiting examples of suitable vehicles include emulsions (e.g., water-in-oil, water-in-oil-in-water, oil-in-water, oil-in-water-in-oil, oil-in-water-in-silicone, water-in-silicone, silicone-in-water emulsions), creams, lotions, solutions (both aqueous and hydro-alcoholic), anhydrous bases (such as lipsticks and powders), gels, and ointments or by other method or any combination of the forgoing as would be known to one of ordinary skill in the art (see, e.g., Remington's, 1990 and International Cosmetic Ingredient Dictionary and Handbook, $10^{th}$ Ed., 2004)). Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes which precipitate from the finished product.

F. Cosmetic Products and Articles of Manufacture

The composition of the present invention can also be used in many cosmetic products including, but not limited to, sunscreen products, sunless skin tanning products, hair products, finger nail products, moisturizing creams, skin benefit creams and lotions, softeners, day lotions, gels, ointments, foundations, night creams, lipsticks, cleansers, toners, masks, or other known cosmetic products or applications. Additionally, the cosmetic products can be formulated as leave-on or rinse-off products. In certain aspects, the compositions of the present invention are stand-alone products.

G. Kits

Kits are also contemplated as being used in certain aspects of the present invention. For instance, emulsion compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the emulsion composition. In other embodiments, the container can be squeezed (e.g., metal, laminate, or plastic tube) to dispense a desired amount of the emulsion composition. The emulsion composition can be dispensed as a spray, an aerosol, a liquid, a fluid, or a semi-solid. The containers can have spray, pump, or squeeze mechanisms. A kit can also include instructions for employing the kit components as well the use of any other emulsion compositions included in the container. Instructions can include an explanation of how to apply, use, and maintain the emulsion compositions.

EXAMPLES

The following examples are included to demonstrate certain non-limiting aspects of the invention. It should be appreciated by those of skill in the art that the techniques disclosed in the examples which follow representative techniques discovered by the inventor to function well in the practice of the invention. However, those of skill in the art should appreciate that changes can be made in the specific embodiments which are disclosed and still obtain a like or similar result without departing from the spirit and scope of the invention.

Example 1

Determining Efficacy of the Guar Gum Containing Compounds as Dispersing Agents

The efficacy of the guar gum containing compounds disclosed throughout this specification as dispersing agents can be determined by methods known to those of ordinary skill in the art. For instance a Hegaman draw-down gauge or a Colorimetric/spectroscopic evaluation (% reflectance vs. wavelength) can be used to measure the dispersion of a colorant in a composition or a phase of a composition. The agglomeration of a colorant can also be analyzed by reviewing the distribution curve of such a colorant in a composition or a phase of a composition.

All of the compounds, compositions, and/or methods disclosed and claimed can be made and executed without undue experimentation in light of the present disclosure. While the compounds, compositions, and methods of this invention have been described in terms of certain embodiments, it will be apparent to those of skill in the art that variations may be applied to the compounds, compositions, and/or methods and in the steps or in the sequence of steps of the method without departing from the concept, spirit and scope of the invention.

More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

REFERENCES

The following references, to the extent that they provide exemplary procedural or other details supplementary to those set forth herein, are specifically incorporated herein by reference.

U.S. Pat. No. 2,798,053

U.S. Pat. No. 4,509,949

U.S. Pat. No. 5,087,445

CTFA International Cosmetic Ingredient Dictionary and Handbook, 10$^{th}$ Ed., (2004). Organic Chemistry, 5$^{th}$ Ed.

Remington's Pharmaceutical Sciences, 18th Ed. Mack Printing Company, 1289-1329, 1990.

The invention claimed is:

1. A method of reducing the appearance of coloring streaks in a composition that has a colorant comprising adding a compound having the following structure to said composition:

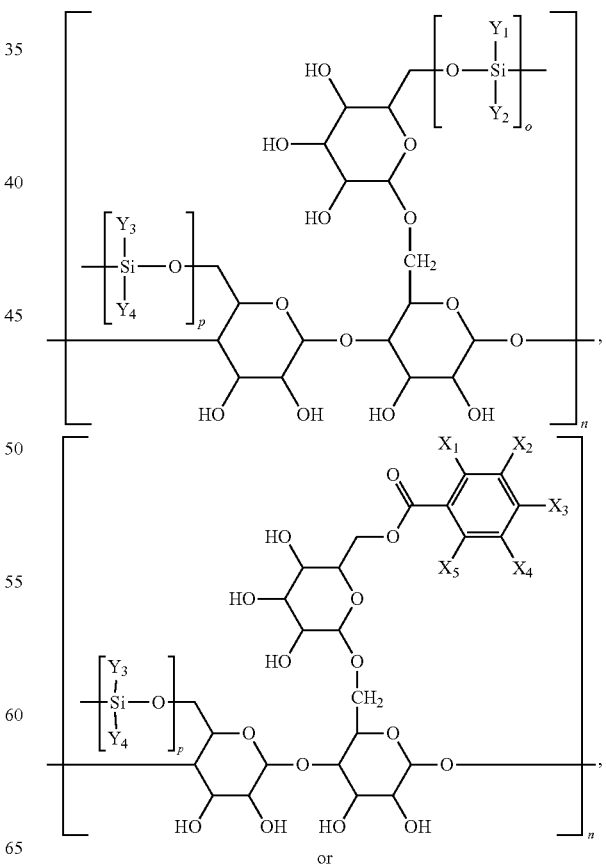

or

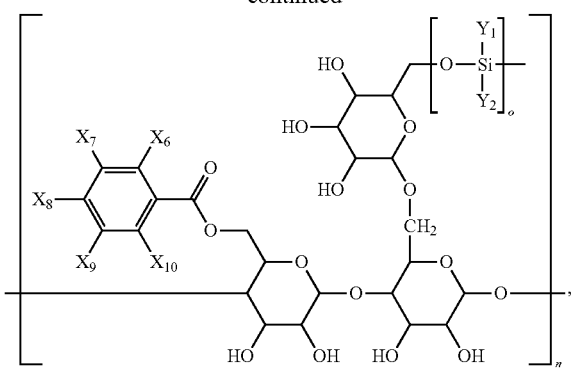

where
- $Y_1$ though $Y_4$ are each independently —H or an alkyl group,
- $X_1$ though $X_{10}$ are each independently —H, —OH, or an alkyl group, and
- N, O, and P are each independently integers is an integer from 2 to 100.

2. The method of claim 1, wherein $Y_1$ through $Y_4$ are each —H.

3. The method of claim 1, wherein $X_1$ through $X_{10}$ are each —H.

4. The method of claim 1, wherein the composition is a cosmetic composition.

5. The method of claim 1, wherein the composition is a mascara, an eyeliner, or a lipstick composition.

* * * * *

UNITED STATES PATENT AND TRADEMARK OFFICE
CERTIFICATE OF CORRECTION

PATENT NO. : 8,158,113 B2
APPLICATION NO. : 13/219324
DATED : April 17, 2012
INVENTOR(S) : Amit Patel It is certified that error appears in the above-identified patent and that said Letters Patent is hereby corrected as shown below:

In claim 1, column 18, line 2, delete "though" and insert --through-- therefor.

In claim 1, column 18, line 4, delete "though" and insert --through-- therefor.

In claim 1, column 18, line 6, delete "is an integer".

Signed and Sealed this
Third Day of July, 2012

David J. Kappos
*Director of the United States Patent and Trademark Office*